United States Patent
Cully et al.

(10) Patent No.: US 8,562,633 B2
(45) Date of Patent: Oct. 22, 2013

(54) TISSUE REPAIR DEVICE WITH A BIOABSORBABLE SUPPORT MEMBER

(75) Inventors: Edward H. Cully, Flagstaff, AZ (US); James T. Walter, Flagstaff, AZ (US); Charles F. White, Camp Verde, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 492 days.

(21) Appl. No.: 10/910,501

(22) Filed: Aug. 2, 2004

(65) Prior Publication Data

US 2006/0025785 A1   Feb. 2, 2006

(51) Int. Cl.
*A61B 17/08* (2006.01)

(52) U.S. Cl.
USPC ............................................. 606/151

(58) Field of Classification Search
USPC ............................................. 606/151
See application file for complete search history.

(56) References Cited

U.S. PATENT DOCUMENTS

| | | | |
|---|---|---|---|
| 3,953,566 A | 4/1976 | Gore | 264/288 |
| 4,187,390 A | 2/1980 | Gore | 174/102 |
| 4,915,893 A * | 4/1990 | Gogolewski et al. | 264/205 |
| 5,019,096 A | 5/1991 | Fox, Jr. et al. | 623/1 |
| 5,116,357 A * | 5/1992 | Eberbach | 606/213 |
| 5,122,155 A | 6/1992 | Eberbach | 606/213 |
| 5,141,515 A * | 8/1992 | Eberbach | 606/151 |
| 5,258,000 A | 11/1993 | Gianturco | 606/151 |
| 5,366,460 A | 11/1994 | Eberbach | 606/151 |
| 5,368,602 A * | 11/1994 | de la Torre | 606/151 |
| 5,370,650 A | 12/1994 | Tovey et al. | 606/151 |
| 5,433,996 A | 7/1995 | Kranzler et al. | 428/247 |
| 5,496,345 A * | 3/1996 | Kieturakis et al. | 606/192 |
| 5,501,661 A | 3/1996 | Cartmell et al. | 602/58 |
| 5,593,441 A | 1/1997 | Lichtenstein et al. | 623/11 |
| 5,607,590 A * | 3/1997 | Shimizu | 210/490 |
| 5,634,931 A | 6/1997 | Kugel | 606/151 |
| 5,695,525 A | 12/1997 | Mulhauser et al. | 623/11 |
| 5,725,577 A | 3/1998 | Saxon | 623/11 |
| 5,743,917 A | 4/1998 | Saxon | 623/11 |
| 5,824,082 A | 10/1998 | Brown | 623/11 |
| 5,916,225 A | 6/1999 | Kugel | 606/151 |

(Continued)

FOREIGN PATENT DOCUMENTS

DE   9012161.9        2/1992
EP   1306061 a2 *    5/2003 .................. 606/151

(Continued)

OTHER PUBLICATIONS

Dualmesh® Plus Biomaterial product brochure "A Legacy of Innovation in Hernia Repair" Jul. 2001. W. L. Gore & Associates, Inc.

(Continued)

*Primary Examiner* — Corrine M McDermott
*Assistant Examiner* — Gregory Anderson
(74) *Attorney, Agent, or Firm* — Amy L. Miller (57) ABSTRACT

The present invention is a composite medical device having a non-bioabsorbable implantable tissue repair or reconstruction component and a resilient bioabsorbable support member component that aids in deployment and placement of the implantable component at a surgical site. Following deployment, the support member component is readily bioabsorbed and removed from the implantable component. The invention is particularly useful in laproscopic, endoluminal, and other surgical procedures.

12 Claims, 11 Drawing Sheets

(56) References Cited

U.S. PATENT DOCUMENTS

| | | | |
|---|---|---|---|
| 5,957,939 A | 9/1999 | Heaven et al. | 606/151 |
| D416,327 S | 11/1999 | Kugel | D24/189 |
| 6,120,539 A * | 9/2000 | Eldridge et al. | 623/11.11 |
| 6,162,537 A * | 12/2000 | Martin et al. | 428/373 |
| 6,165,217 A | 12/2000 | Hayes | 623/11.11 |
| 6,171,318 B1 | 1/2001 | Kugel et al. | 606/151 |
| 6,174,320 B1 | 1/2001 | Kugel et al. | 606/151 |
| 6,176,863 B1 | 1/2001 | Kugel et al. | 606/151 |
| 6,224,616 B1 | 5/2001 | Kugel | 606/151 |
| 6,241,768 B1 * | 6/2001 | Agarwal et al. | 623/11.11 |
| 6,264,604 B1 | 7/2001 | Kieturakis et al. | 600/207 |
| 6,280,453 B1 * | 8/2001 | Kugel et al. | 606/151 |
| 6,302,897 B1 | 10/2001 | Rousseau | 606/190 |
| 6,309,423 B2 | 10/2001 | Hayes | 623/23.75 |
| 6,436,030 B2 * | 8/2002 | Rehil | 600/37 |
| 6,551,356 B2 * | 4/2003 | Rousseau | 623/23.72 |
| 6,599,323 B2 * | 7/2003 | Melican et al. | 623/23.72 |
| 6,669,735 B1 | 12/2003 | Pelissier | |
| 6,736,823 B2 * | 5/2004 | Darois et al. | 606/151 |
| 6,755,867 B2 * | 6/2004 | Rousseau | 623/23.64 |
| 6,800,082 B2 * | 10/2004 | Rousseau | 606/151 |
| 2003/0078602 A1 * | 4/2003 | Rousseau | 606/151 |
| 2004/0019360 A1 * | 1/2004 | Farnsworth et al. | 606/151 |
| 2004/0092969 A1 * | 5/2004 | Kumar | 606/151 |
| 2004/0172048 A1 | 9/2004 | Browning | |

FOREIGN PATENT DOCUMENTS

| | | |
|---|---|---|
| JP | 2002/522112 A | 7/2002 |
| JP | 2002/272833 A | 9/2002 |
| WO | 02/078568 | 10/2002 |
| WO | 2004/010896 | 2/2004 |

OTHER PUBLICATIONS

Supplementary European Search Report, EP 05777404, Apr. 21, 2011, 2 pages.

* cited by examiner

TISSUE REPAIR DEVICE WITH A BIOABSORBABLE SUPPORT MEMBER

FIELD OF THE INVENTION

The present invention relates to implantable medical devices. In particular, the invention is directed to a composite implantable medical device having an implantable tissue repair component and a component that assists in deployment of the tissue repair component at a surgical site and is subsequently removed by being bioabsorbed.

BACKGROUND OF THE INVENTION

Implantable medical devices designed to help repair damaged tissues have been successfully used for years. Some of these devices are used to patch damaged tissue and provide mechanical support to the tissues during healing. A simple form of these devices is a flexible patch-like sheet. The composition and morphology of the sheets are usually tailored to address a particular surgical need. In some cases, it is desirable to incorporate a reinforcing element into the flexible sheets. In addition to mechanical support, reinforcing elements often assist in handling and deployment of the implantable sheet devices. Ease of handling and deployment of flexible sheet devices are particularly desired when laproscopic instruments and procedures are used to implant the devices.

An example of one of these devices is disclosed by de la Torre in U.S. Pat. No. 5,368,602. de la Torre describes a patch made of a surgical mesh material having one or more semi-rigid frame-like support elements permanently secured to the mesh material along all or part of the border of the material. The semi-rigid support members are said to enable manipulation and positioning of the entire mesh area with conventional laproscopic instruments.

U.S. Pat. No. 5,695,525, issued to Mulhauser et al., discloses a semi-rigid framework in the form of a ring permanently attached to one side of a planar mesh material. The support ring is designed to prevent the planar mesh material from collapsing into crater-like defects in tissue by maintaining the mesh material in an expanded configuration across the defect site.

A repair patch similar to the Mulhauser et al. device is disclosed in U.S. Pat. No. 5,824,082, issued to Brown. The Brown patch utilizes a framework made of a metallic support wire. The support wire has shape-memory properties. The support wire is permanently attached to a preformed patch material along its periphery. The shape-memory characteristic of the support wire enables the repair patch to be rolled into a small cylindrical profile at room temperatures and alter its configuration to expand and flatten the patch material at body temperatures. The repair patch is said to reside between layers of tissue at a repair site and not require sutures or staples.

In U.S. Pat. No. 6,280,453, issued to Kugel et al., a hernia repair patch is disclosed having the form of a laminated mesh material with a framework made of a resilient monofilament spring permanently located between layers of the laminate. Once the patch is placed through an incision site in a hernia patient, the spring element assists in unfolding and expanding the patch into a planar configuration. The patch is provided with a pouch into which a surgeon can place a finger to position the patch across a hernia, rather than having to use a laproscopic instrument to position the patch.

A variation on the theme of implantable tissue repair devices having permanently attached reinforcing frameworks is disclosed by Gianturco in U.S. Pat. No. 5,258,000. The Gianturco device is initially implanted as an unsupported flexible bag having an internal space into which an elastic stiffener wire is subsequently threaded. The stiffener wire causes the bag to adopt a flattened shape. The flattened repair device with its stiffener wire is permanently secured to tissue surrounding the repair site with sutures or staples.

In surgical procedures that utilize a tissue repair material with a stiffener element, it may be desirable to remove the stiffener element from the repair material following at least partial attachment of the repair material to tissues of the repair site. In U.S. Pat. No. 5,370,650, issued to Tovey et al., an apparatus for positioning tissue repair meshes adjacent to body tissue is disclosed. The apparatus includes a delivery device with an arm that extends to place the tissue repair mesh into a surgical site. The arm has a stiffener element for the tissue repair mesh attached to its distal end. The tissue repair mesh is secured to the stiffener element with sutures sewn around the stiffener element and through holes in the mesh. The sutures can be sewn in such a way as to permit removal of the sutures from the tissue repair mesh following deployment. Prior to removal of the sutures from the mesh material, at least a portion the mesh material can be secured to tissues of the surgical site with sutures or staples. Once the tissue repair mesh is in place, the sutures holding the mesh to the stiffener element are removed. The delivery device is then separated from the tissue repair mesh and extracted from the surgical site.

A pneumatically operated deployment device for a tissue repair mesh is disclosed in U.S. Pat. No. 6,302,897, issued to Rousseau. The Rousseau device is an applicator with a tissue repair mesh simply placed on an external surface of an inflatable bladder. The bladder has two portions. The first portion is filled with air. The second portion is initially empty, but is fillable with the air from the first portion when external mechanical pressure is applied to the first portion. As the second portion is inflated, the applicator and tissue repair mesh are unfolded and the repair mesh pressed against a patient's tissue. Following deployment of the mesh, the bladder is removed from the surgical site by hand.

Farnsworth, et al. in U.S. Patent Publication No. 2004/0019360 disclose a tissue implant reinforced with a removable support member. The removable support member aids in placement and deployment of the tissue implant at an implantation site. The tissue implant and removable support member are both made of non-bioabsorbable materials.

In some applications, it would be useful to eliminate the need to remove a reinforcing member from a tissue repair device or material. In U.S. Pat. No. 6,599,323, Melican, et al. disclose a bioabsorbable tissue implant reinforced with a component that can be bioabsorbable for use in pelvic floor repair. The tissue implant comprises one or more layers of a bioabsorbable polymeric foam having pores with an open cell structure. The tissue implant is in the form of a porous foam material. The foam component is integrated with the reinforcing component such that the pores of the foam component penetrate the mesh of the reinforcing component and interlock with the reinforcing component. Melican et al., teach implants, such as patches, made from non-bioabsorbable material are undesirable, however.

None of these devices recognize the advantages of providing a non-bioabsorbable implantable sheet material with a resilient support member that is bioabsorbable. Such a device would have an adhesion scheme that permits the resilient support member to be initially held in place on the implantable sheet material with sufficient strength to withstand placement within and delivery from a laproscopic or similar surgical instrument. Yet the resilient support member would be removed from the implantable sheet material through a bioabsorption process and would not require further surgical procedures to remove the support member from the surgical site.

The bioabsorbable resilient support member would assist in changing the implantable sheet material from a compacted configuration to a more planar configuration. The support member could also provide an unobstructed border area in which a complete set of sutures or staples encompassing the non-bioabsorbable repair material could be put in place and tested. Such a device would optionally include features that assist in tactile and visual orientation of the device at a surgical site. The bio-absorbable support member could be combined with bioactive compounds that would be released at the implantation site independently or in combination with bio-absorption of the support member.

SUMMARY OF THE INVENTION

The present invention is directed to a medical device for use in repair or reconstruction of damaged tissue as well as other surgical procedures. The device is particularly suited for repair of hernias and similar tissue damage requiring surgical placement and fixation of a patch-like material at the repair site. A bio-absorbable support member is attached to the patch-like device to enable a rolled device to unroll, or self-expand, at an implantation site without the need for an extrinsically applied force or a thermal transition of the support member material.

The invention has two principle components. One component is an implantable device made of a non-bioabsorbable material, preferably in a planar form. The other component is a resilient polymeric support member made of a bioabsorbable material designed to assist in deployment and positioning of the implantable device at a surgical site. The bioabsorbable resilient support member is attached to the implantable device in such a way as to permit bioabsorption of the support member by the body of the implant recipient. The resilient support member is bioabsorbed by enzymatic action and/or hydrolysis of the polymeric material comprising the support member through physiological processes of the implant recipient. As a consequence, removal of the support member from the implantable device does not require a further surgical step, or procedure. The bioabsorbale resilient support member is also preferred in planar form.

Figures 4A, 4B:
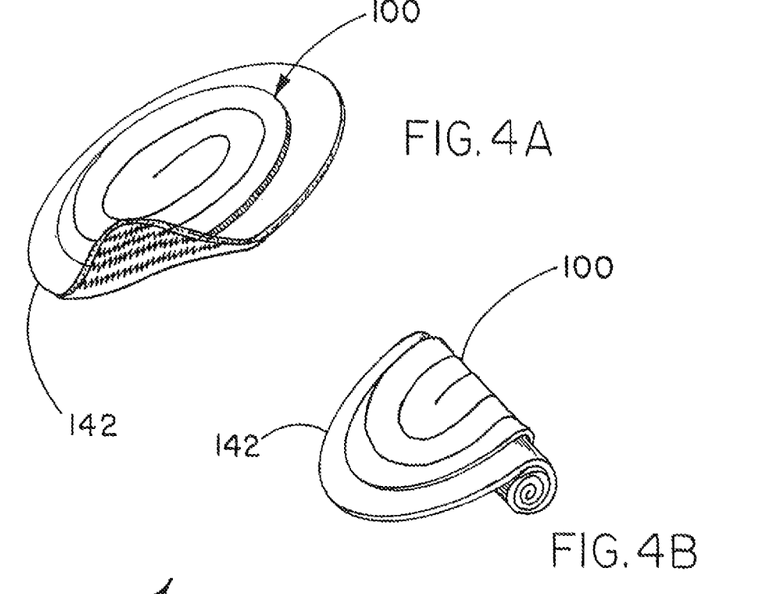
FIGS. 4A-4D illustrate the present invention being compacted, unrolled, and afixed with surgical fasteners.
Figures 4C, 4D:
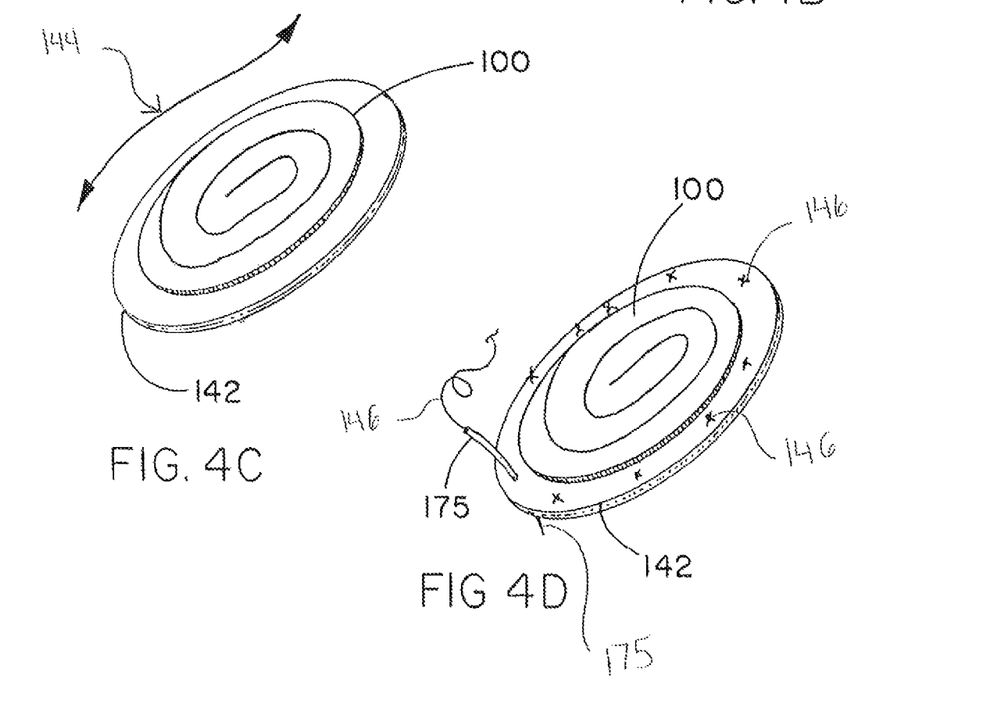

The combined planar materials are sufficiently pliable to permit the invention (FIG. 4A) to be rolled, folded, or otherwise compacted in form (FIG. 4B) and delivered with laproscopic instruments or other conventional surgical techniques. Following delivery of the invention to a surgical site, the bioabsorbable resilient support member readily recovers from the compacted form to substantially return to its original planar form. As the support member returns to its original planar form, the resilience of the support member causes the attached implantable device to readily change from the compacted form to the original planar configuration. As the invention assumes a planar form at a surgical site (FIG. 4C, arrow (144)), the bioabsorbable support member enables the implantable sheet material to be easily manipulated, positioned, and secured to tissues of the surgical site with surgical fasteners (146), which may be positioned by a surgical needle (175) (FIG. 4D). Once the implantable device is secured, the surgical procedure is concluded.

Figure 1:
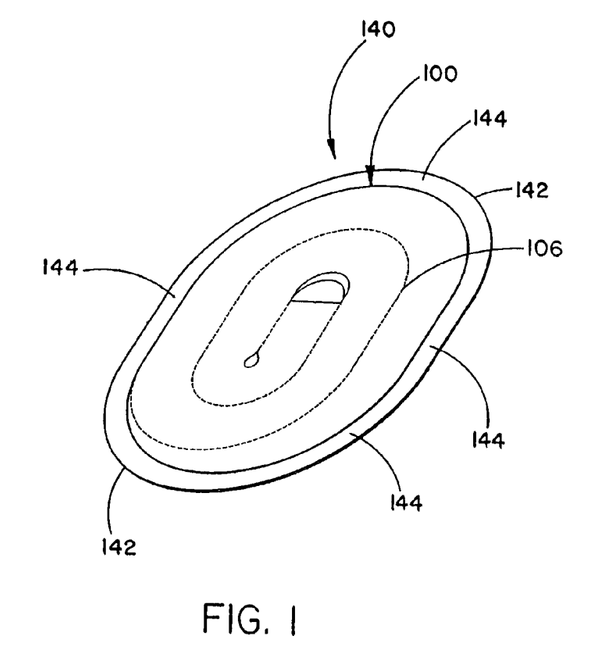
FIG. 1 illustrates an isometric view of the present invention.
Figure 2A:
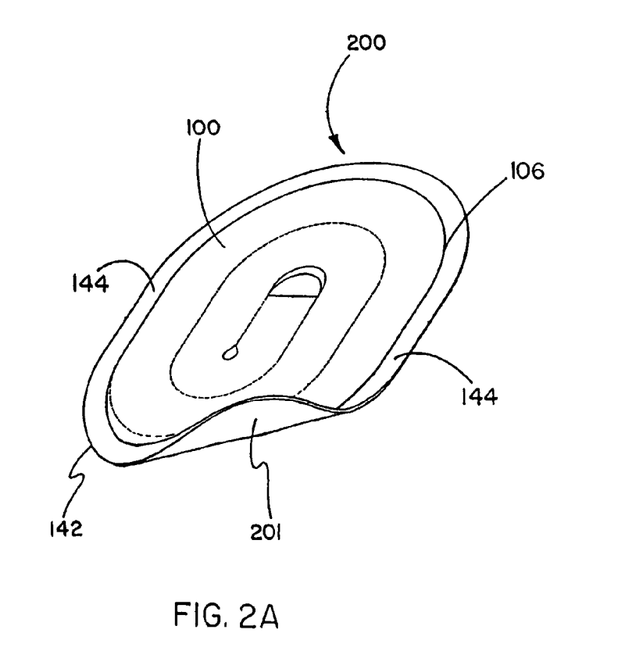
FIG. 2A illustrates a perspective view of the present invention with a corner of the implantable sheet material folded up to show a smooth texture of one surface of the sheet material.
Figure 2B:
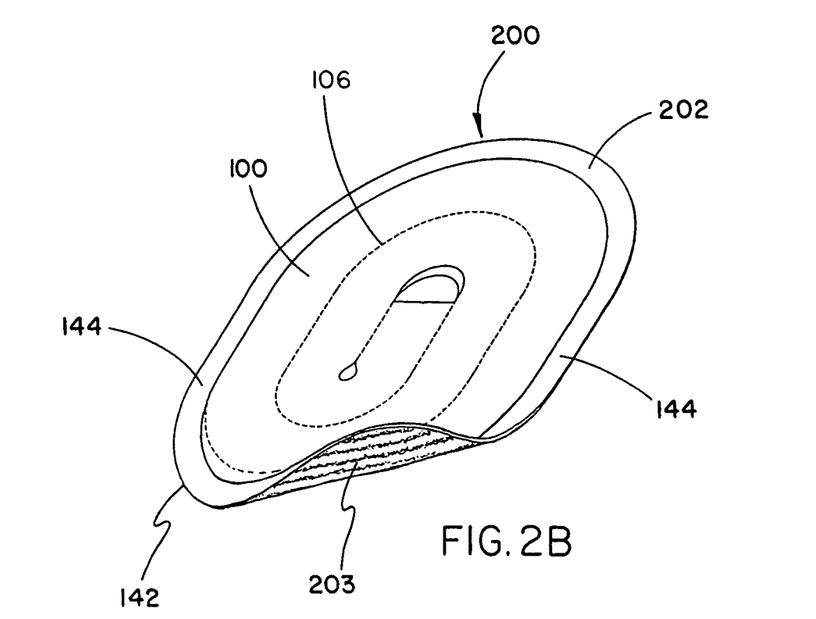
FIG. 2B illustrates a perspective view of the present invention with a corner of the implantable sheet material folded up to show a roughened texture of one surface of the sheet material.
Figure 2C:
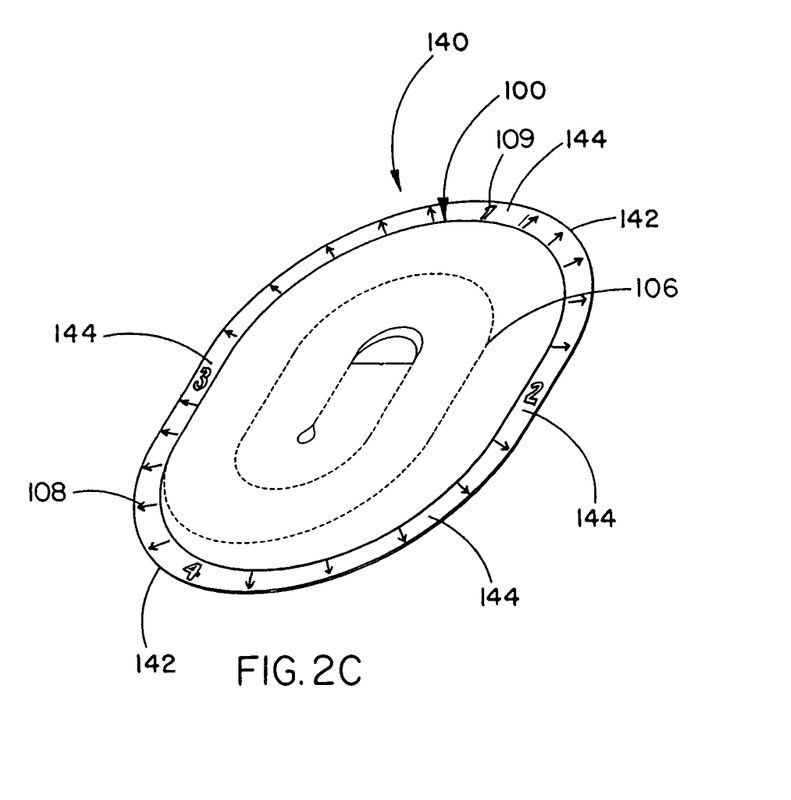
FIG. 2C illustrates a perspective view of the present invention with reference characters in the border area of the implantable device.
Figure 3:
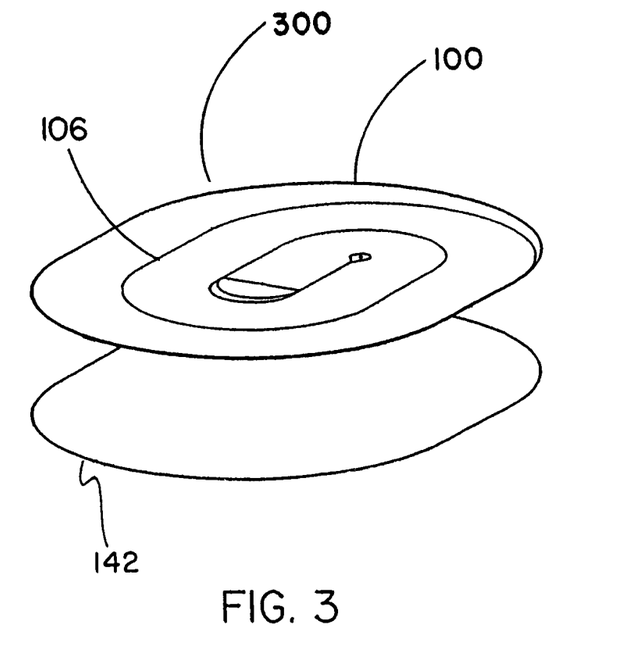
FIG. 3 illustrates an exploded view of the present invention where the support member and the implantable sheet material are essentially the same size.
Figure 3A:
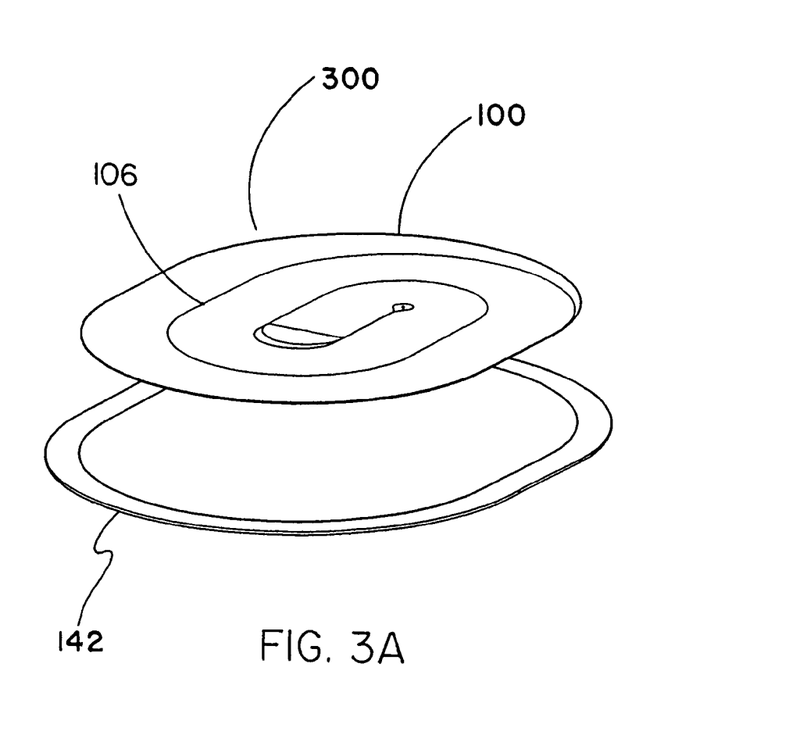
FIG. 3A illustrates an exploded view of the present invention.
Figure 3B:
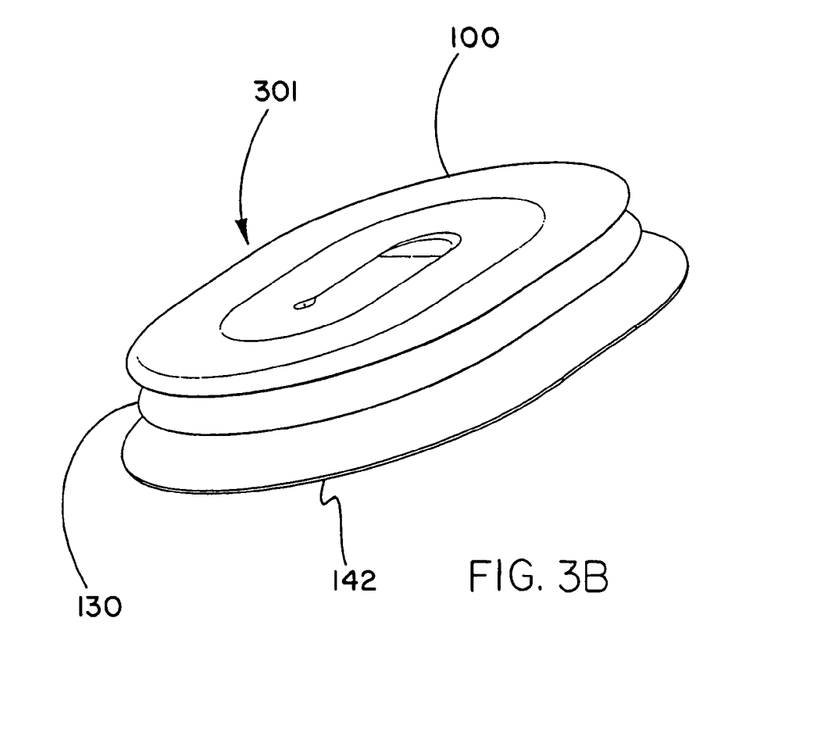
FIG. 3B illustrates an exploded view of the present invention with an adhesive agent applied between the support member and the implantable sheet material.

In preferred embodiments, the bioabsorbable support member is sized to entirely cover the non-bioabsorbable implantable sheet material (FIG. 3). In other embodiments, the bioabsorbable support member covers only part of the surface area of the implantable device (FIGS. 2, 2A, 2B, 5-7, et al.). This leaves the border area of the implantable device exposed and available for fixation with sutures, staples, tacks, or other surgical fasteners. In these and other embodiments, the present invention can have letters, numbers, and other characters or features that aid in visual orientation of the invention with respect to a surgical repair site. A particularly preferred visual aid involves the use of different colors for the implantable device and the support member. In addition to the visual aids, the support member can be constructed to provide tactile distinctions between different sides of the invention as well as tactile distinctions between the implantable device and the support member.

One embodiment of the present invention is a medical device comprising a resilient bioabsorbable support member, and an implantable non-bioabsorbable device attached to said resilient bioabsorbable support member, wherein said resilient bioabsorbable support member assists in deployment and placement of said non-bioabsorbable implantable device during implantation procedures without requisite for an extrinsically applied force. In addition, the polymeric material of the bioabsorbable support member does not undergo a thermal transition during deployment (i.e, expansion, unrolling, etc.) of the medical device.

Although generally planar sheet materials are preferred in the present invention, filamentous materials in mesh, woven, or non-woven forms are also contemplated in the invention as well as composites thereof. The composites can be arranged so the bio-absorbable support member is placed on one or more surfaces of the tissue implant material. Alternatively, the bio-absorbable support member can be placed between two or more layers of tissue implant material. The layers of tissue implant material can be made of the same or different materials. The structure of these materials can be selected to influence bioabsorption rates of the polymeric material of the support member. For example, porous materials limit the rate at which a compound can move into and through pores of the material. A hydrophobic porous material, such as porous expanded polytetrafluoroethylene (ePTFE), also delays entry of aqueous fluids through the material to the hydrolyzable polymeric material of the support member. Delaying the contact of an aqueous fluid with the support member, delays bioabsorption of the support member. In addition to the composition, structure, and inter-relationship of these materials, the dimensions of the materials can be varied to achieve a desired bioabsorption profile.

The bioasbsorption rate of the polymeric material of the support member can be further influenced by varying the geometry of particular parts of the support member. For example, a dimension of at least one portion of the support member can be tapered to present less polymer mass at one location than another location on the support member. Portions of the support member having less polymer mass are absorbed more easily and rapidly than portions of the support member with more polymer mass.

The chemical composition of particular parts of the support member can also be varied to influence bioabsorption rates of the polymeric material. The bioabsorption rates of a non-blended hydrolyzable co-polymer suitable for use in the present invention can be influenced by the ratio and location of one polymer to the other polymer in the co-polymer in the polymeric chain. Different non-blended hydrolyzable co-polymers can be used in different portions of the support member. One embodiment is made from sheets each having a different non-blended hydrolyzable co-polymer composition. Pieces of each sheet are cut out and arranged together to form a support member of the present invention having regions, or zones, exhibiting different rates of bioabsorption.

Of further note, coverings, geometric design and zones of differing copolymer ratios may be combined within the same device to achieve desired rates of bioabsorbtion and biological performance.

Each embodiment of the present invention can have an anti-microbial agent associated therewith.

Other features of the present invention will become apparent from the following detail description of the invention when taken in connection with the accompanying drawings. It is understood that the drawings are designed for the purpose of illustration only and are not intended as a definition of the limits of the invention.

DETAILED DESCRIPTION OF THE INVENTION

The preferred medical device of the present invention is a composite of a resilient bioabsorbable support member attached to a implantable sheet of flexible non-bioabsorbable polymeric material suitable for use as a tissue repair material. Both components of the preferred composite have a planar form.

As seen in FIG. 2, for example, the preferred implantable device of the present invention (140) is a generally planar sheet of flexible, tissue-compliant, non-bioabsorbable biocompatible polymeric material (142). Suitable polymeric materials include, but are not limited to, polypropylene, polyethylene, nylon, and polytetrafluoroethylene. The preferred polymeric material is an expanded, porous, polytetrafluoroethylene made according to U.S. Pat. Nos. 3,953,566 and 4,187,390, both issued to Gore. There are two implantable sheet materials that are most preferred. One most preferred implantable sheet material is a tissue repair patch made of porous expanded polytetrafluoroethylene (ePTFE) available from W. L. Gore & Associates, Inc., Medical Products Division, Flagstaff, Ariz. under the tradename GORE-TEX® DUALMESH® Biomaterial as part number 1DLMC04. The other most preferred implantable sheet material is a porous expanded polytetrafluoroethylene (ePTFE) material with an anti-microbial agent associated therewith. An antimicrobial treatment may be provided on the implantable sheet per, for example, U.S. Pat. No. 5,019,096 issued to Fox, Jr., et al. The final product is available from W. L. Gore & Associates, Inc., Medical Products Division, Flagstaff, Ariz. under the tradename GORE-TEX® DUALMESH® PLUS Biomaterial as part number 1DLMCP04. These most preferred materials have an oval shape with sizes in a range from 7.5 cm×10.0 cm to 26.0 cm×34.0 cm. Other planar shapes such as circles, squares, triangles, and custom-fitted shapes are also contemplated for use in the present invention. Regardless of the shape, suitable implantable sheet materials range in size from as small as 1.0 cm×1.0 cm to as large as 50.0 cm×50.0 cm, with 5.0 cm×5.0 cm to 40.0 cm×40.0 cm sized pieces being preferred, and pieces in a range from about 7.0 cm×7.0 cm to about 20.0 cm×20.0 cm being most preferred.

Suitable polymeric materials for the bioabsorbable support member include, but are not limited to a block co-polymer of polyglycolic acid and trimethylene carbonate (PGA/TMC), polylactic acid/polyglycolic acid (PLA/PGA), or other homopolymers, copolymers, or polymeric blends derived from other biocompatible bioabsorbable monomeric components. Such homopolymers or copolymers can be comprised of varying amounts of one or more of the following monomer examples: glycolide, d,l-lactide, l-lactide, d-lactide, p-dioxanone (1,4-dioxane-2-one), trimethylene carbonate (1,3-dioxane-2-one), $\epsilon$-caprolactone, gamma.-butyrolactone, delta.-valerolactone, 1,4-dioxepan-2-one, and 1,5-dioxepan-2-one. Other bioabsorbable polymeric constituents may include polyethylene glycol, polypropylene glycol, N-vinyl pyrrolidone, amino acids, anhydrides, orthoesters, phosphazines, amides, urethanes, and phosphoesters. Alternative copolymers may possess, in whole or in part, combinations of block, segmented, random, alternating, or statistical polymeric construction characteristics.

The preferred polymeric material is a semi-crystalline segmented block copolymer of 67% PGA:33% TMC. The ratios of the PGA:TMC constituents can be adjusted during synthesis to alter the mechanical strength, bioabsorption rates, and processability of the co-polymer.

The preferred polymeric material is PGA/TMC. The ratios of the PGA/TMC constituents can be adjusted during synthesis to alter the mechanical strength, bioabsorption rates, and processability of the co-polymer. Of particular significance with respect to the present invention is the ability of PGA/TMC co-polymers to change in shape from a compacted, or rolled, configuration to an uncompacted, or flattened, configuration without undergoing a thermal transition. Accordingly, devices of the present invention can be introduced, self-expanded, or unraveled, and secured at normal human body temperatures, or below.

In some embodiments, the resilient bioabsorbable support member has a surface area less than the surface area of the implantable sheet material and lies within the perimeter of the implantable sheet material. This arrangement provides an unobstructed border area (144) on the implantable sheet material (142) that circumscribes the support member (100). The border area is available for sutures, staples, tacks, and/or other surgical fasteners. Useful border widths range from 0.3 cm to about 3.0 cm, with a preferred range from 0.5 cm to 2.0 cm, and a most preferred range between 0.8 cm to 1.2 cm.

Figure 11:
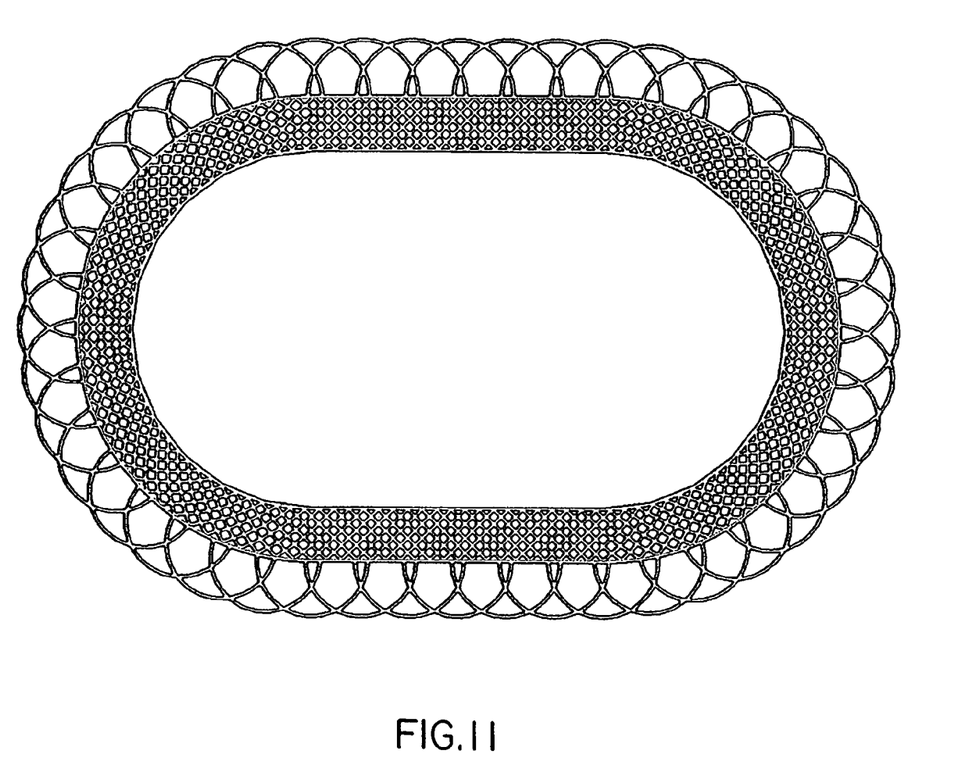
FIG. 11 illustrates a top view of a bioabsorbable support member of the present invention.

The resilient bioabsorbable support member preferably has the same outer dimensions as the implantable non-bioabsorbable sheet material (FIG. 3). In the most preferred embodiment, a bioabsorbable support member having the pattern shown in FIG. 11 is sized to cover the entire surface are of a non-bioabsorbable sheet material without forming a border area.

Figure 4G:
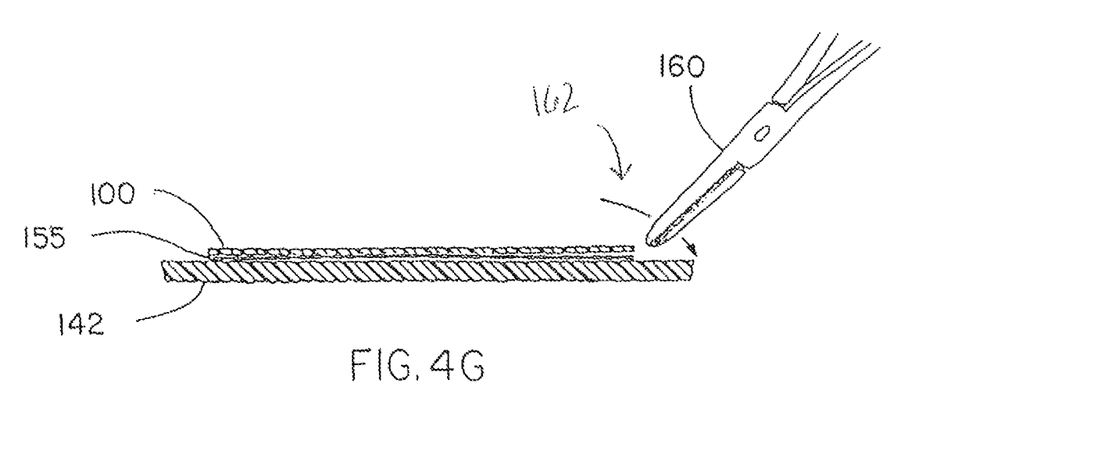
FIG. 4G illustrates a cross-section of the present invention with a support member of sufficient thickness to provide a tactile step.
Figures 5, 6, 7:
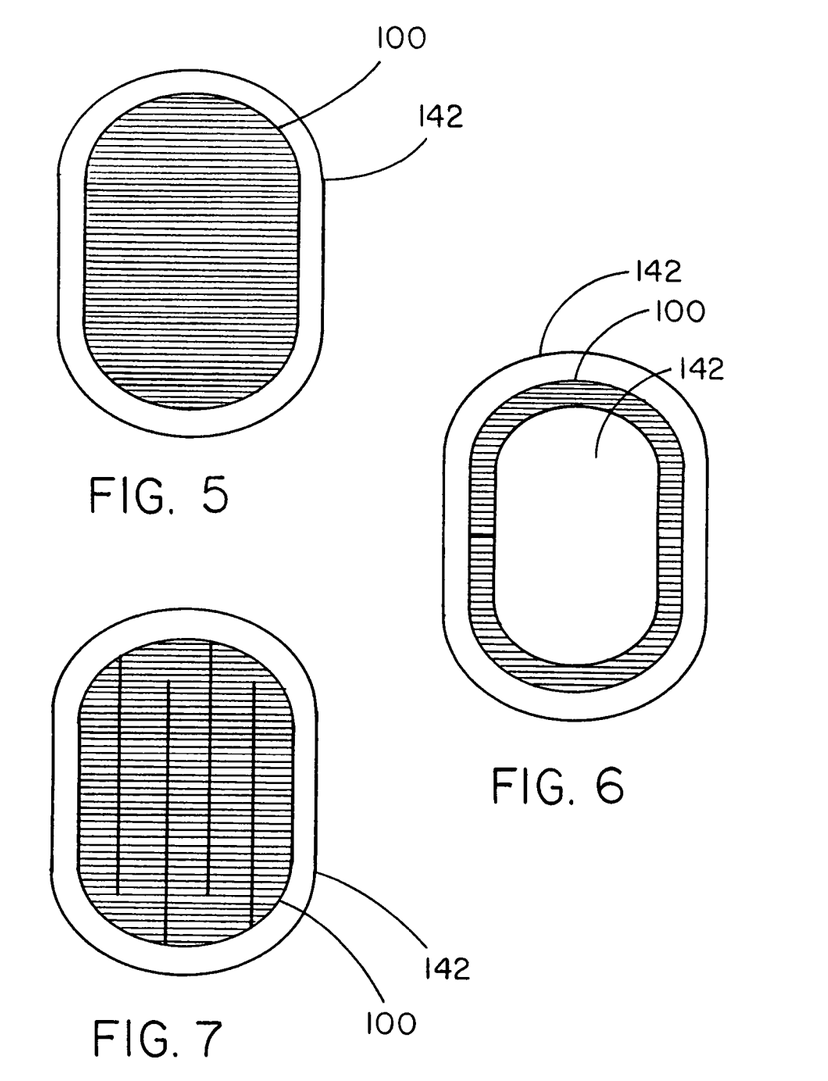
FIGS. 5-7 illustrate different bio-absorbable support member configurations attached to implantable materials of the present invention.

With resilient bioabsorbable support members having a thickness in a range from about 0.05 mm to about 2.0 mm, the thickness of the resilient bioabsorbable support member can serve as an important feature of the present invention. During laproscopic procedures, for example, a clearly perceivable tactile change is felt when manually operated surgical instruments (160) are moved across the surface of the resilient bioabsorbable support member and dropped off an edge of the support member onto the implantable sheet material (FIG. 4G, arrow (162)). A surgeon can take advantage of this "tactile step" to detect the border area of the implantable sheet material by feel. Knowing the location of the border area of the implantable sheet material permits the surgeon to confine placement of surgical fasteners to the border area and refrain from placing fasteners through the bioabsorbable support member.

In addition to a tactile step, differences in surface characteristics between the implantable sheet material and the bioabsorbable support member material can also provide additional tactile feedback to a surgeon. These tactile characteristics include, but are not limited to, surface texture, hardness, and/or lubriciousness.

Adhesion of the bioabsorbable support member to the implantable sheet material is preferably accomplished by softening the surface of the bioabsorbable support member that interfaces with the device through the application of solvents or heat.

In addition to softening the bioabsorbable polymer material of the support member to attach the support member to the implantable sheet material, the bioabsorbable support member can adhered to the implantable sheet material with a bio-absorbable adhesive. Examples of the bio-absorbable adhesives include, but are not limited to, fibrin glue, collagen, a solution of polylactic acid-polyglycolic acid (PLA:PGA) copolymers carried in a suitable solvent and allowed to dry. Suitable bioabsorbable polymeric materials include, but are not limited to amorphous copolymers of PLA:PGA, or other homopolymers, copolymers, or polymeric blends derived from other biocompatible bioabsorbable monomeric components. Such homopolymers or copolymers can be comprised of varying amounts of one or more of the following monomer examples: glycolide, d,l-lactide, l-lactide, d-lactide, p-dioxanone (1,4-dioxane-2-one), trimethylene carbonate (1,3-dioxane-2-one), $\epsilon$-caprolactone, gamma.-butyrolactone, delta.-valerolactone, 1,4-dioxepan-2-one, and 1,5-dioxepan-2-one. Other bioabsorbable polymeric constituents may include polyethylene glycol, polypropylene glycol, N-vinyl pyrrolidone, amino acids, anhydrides, orthoesters, phosphazines, amides, urethanes, and phosphoesters. Copolymers may possess, in whole or in part, combinations of block, segmented, random, alternating, or statistical polymeric construction characteristics.

Adhesion is a complex subject involving combined mechanical and physico-chemical phenomena operating simultaneously with any given adhesive or adhesion scheme. Accordingly, no single theory is adequate to explain adhesion. Generally speaking, however, adhesives work by one of two mechanisms. The first mechanism is based on a thermodynamic model attributed to Sharpe and Schonhorn (L. H. Sharpe and H. Schonhorn, *Chem. Eng. News* 15:67 (1963)). The model is based on a belief that interatomic and intermolecular forces established at an interface between a substrate and an adhesive cause the adhesive to adhere to the substrate. The most common interfacial forces are thought to result from van der Waals and Lewis acid-base interactions. Adequate wetting of the substrate surface with an adhesive is another important aspect of forming adhesive bonds. With regard to the present invention, releasable adhesive bonds include formation of physico-chemical bonds between the bioabsorbable support member, the implantable sheet material, and the adhesive (or within the adhesive itself) that are capable of holding the substrate materials together during implantation procedures.

The other adhesion mechanism is a mechanical interlocking, or anchoring, of an adhesive material with cavities, pores, asperities, or other surface topographies of a substrate material (J. W. MacBain and D. G. Hopkins, *J. Phys. Chem.* 29:88 (1925)). Porous materials may also have subsurface openings that become filled and interlocked with an adhesive material.

Though distinct in theory, both of these mechanisms are operable in forming most adhesive bonds, albeit to different degrees.

Figure 9:
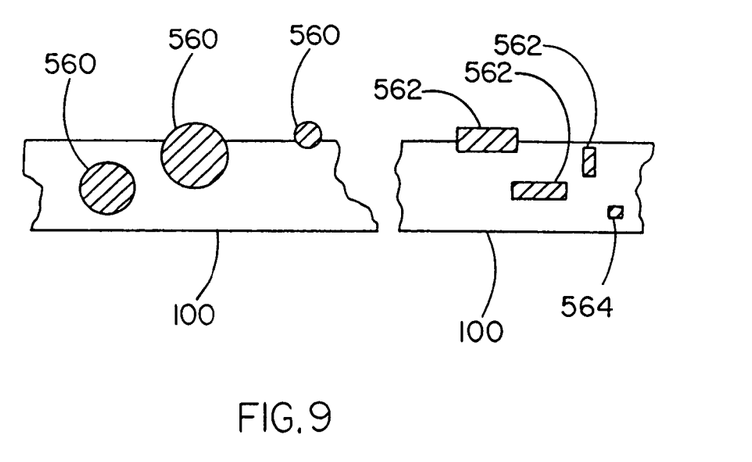
FIG. 9 illustrates two partial cross-sectional views of bioabsorbable support members of the present invention embedded or covered with another material. The additional material can effect bio-absorption rates of the support member and/or release rates of bioactive compounds incorporated into the invention.

The support member component (100) of the present invention (FIG. 2, et seq.) is made of a resilient bioabsorbable polymeric material in generally planar form. The bioabsorbable support member can be constructed of a single material or plurality of materials in the form of a composite. The resilience of the bioabsorbable support member can be an inherent property of the polymeric material or supplied to the polymeric material with a framework structure. Shown in FIG. 9 are partial cross sectional views of support members 100 incorporating various framework structures. Shown are circular shaped framework structures 560 embedded within the support member 100. Also shown are rectangular framework structures 562 and a square framework structure 564, all embedded within the support member 100, support structures 560, 562, 564 can have any cross section shape in order to supply resilience to the support member. For example, a bioabsorbable support member can have an essential, circular, oval, triangle, square, rectangle or other polygon cross section. The bioabsorbable support structure can also be formed from composites, laminates, weaves, yarns or other suitable forms.

Figure 10:
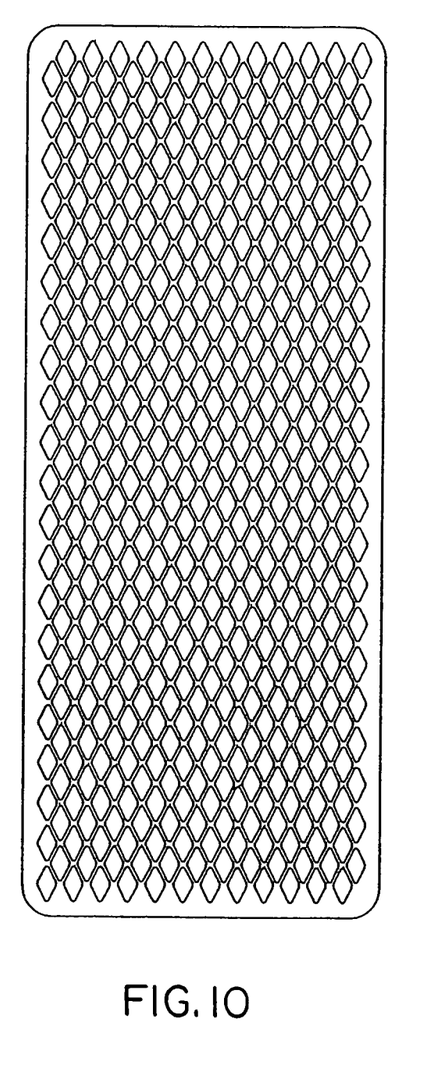
FIG. 10 illustrates a top view of a bioabsorbable support member of the present invention.

While various forms are contemplated for the resilient bioabsorbable support member (FIGS. 5-7), the preferred form is illustrated in FIG. 11. Another preferred form for the bioabsorbable support member is illustrated in FIG. 10. Regardless of the shape and size of the bioabsorbable support member, the support member can be attached to either, or both, sides of a non-bioabsorbable sheet material.

Additional material can be added to the present invention to alter the performance of the invention. For example, a layer of a porous hydrophobic non-biodegradable material such as ePTFE can be placed over the bioabsorbable support member as a barrier to aqueous fluids. Such a hydrophobic barrier would delay aqueous fluids from contacting and hydrolyzing the bioabsorbable support member. Delaying bio-absorption of the support member would allow the support member to function for a longer period as a support before loosing mechanical strength due to the bio-absorption process. In other embodiments, the bio-absorbable support material is coated with other polymeric materials that impact the mechanical strength of the support material and/or the absorption rate of the support material.

Bioactive compounds can be incorporated into the bioabsorbable and/or non-bioabsorbable component of the present invention for release following implantation. Additional layers of materials could be used to control release rates of the bioactive compounds and/or absorption rates of the invention.

These various features can be selected and combined in a single device to provide "programmed" rates of bio-absorption and bioactive compound release that are optimized for a particular application (FIG. 9).

EXAMPLES

Example 1

This example describes the construction of a preferred embodiment of the present invention. Following formation of a non-bioabsorbable implantable sheet material, a bioabsorbable support member was attached to the implant as follows.

The bioabsorbable support member was fabricated from a flat sheet of medical grade block co-polymer of polyglycolic acid-trimethylene carbonate (PGA/TMC) in a 67:33 ratio; respectively. The PGA:TMC copolymerization is achieved by a sequential addition ring opening polymerization of the cyclic trimethylene carbonate and glycolide dimer monomers. Synthesis of PGA:TMC can be conducted to produce copolymers in segmented and/or simple block form. Methods for PGA:TMC synthesis are described in U.S. Pat. Nos. 4,243,775 and 4,300,565 both to Rosensaft, et al and U.S. Pat. No. 4,429,080 to Casey, et al., each of which is incorporated herein by reference.

Other desirable copolymeric ratios and/or block structures may necessitate the use of different variations in polymerization conditions and/or methods. Both glycolide and trimethylene carbonate monomers are available from BI Chemicals, Petersburg, Va. USA. A 33% weight to weight ratio of TMC to PGA segmented triblock copolymer may be obtained from United States Surgical, a unit of Tyco Healthcare Group LP, Norwalk, Conn.

The flat sheet was cut into the pattern shown in FIG. 11 with a perforating $CO_2$ laser system (Laserage Technology Corp, Waukegan, Ill.). The bioabsorbable support member was sized to cover the implantable sheet material without a border area.

An expanded polytetrafluoroethylene (ePTFE), 15 cm×19 cm oval hernia repair patch, tradenamed GORE-TEX® DUALMESH® Biomaterial available from the Medical Products Division of W. L. Gore & Associates, Inc. (Flagstaff, Ariz.) as part number 1DLMC04 was obtained. As seen in FIG. 2B, the GORE-TEX® DUALMESH® Biomaterial product (142) has a different texture (203) on each side of the sheet. One side (202) is designed to prevent or limit tissue adhesions or other tissue attachments thereto. The other side (203) is roughened to encourage tissue attachment or ingrowth of cells or cellular process therewithin.

Figure 8:
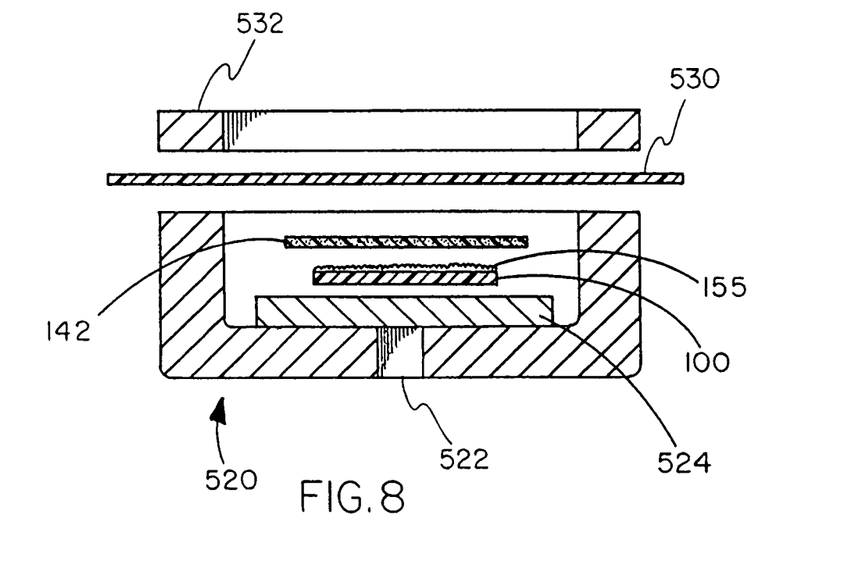
FIG. 8 illustrates a cross-sectional view of a vacuum-laminating press useful in making the present invention.

Once the ePTFE sheet was obtained and the bioabsorbable support member was fabricated, the two were attached by coating the interface surfaces with a solution of polylactic acid-polyglycolic acid (PLA:PGA) in a ratio of 85:15, respectively which was rendered into liquid form by dissolving in acetone. The GORE-TEX® DUALMESH® Biomaterial was oriented so that the "tissue adhesion barrier" side (202) was against the bioabsorbable support member (530). Though the bioabsorbable support member could have been placed on the non-tissue adhesion side of the GORE-TEX® DUALMESH® Biomaterial. Once the surfaces were coated, the components were pressed and held together between aluminum shims on a flat block (FIG. 8). The assembly was allowed to dry overnight.

The result was an implantable medical device of the present invention comprising a non-bioabsorbable implantable sheet material attached to a bioabsorbable support member that is self-expandable in situ without the need for an extrinsically applied force or a thermal transition of the support member material.

Example 2

This example describes the construction of a resilient polymeric bioabsorbable support member attached to a non-bioabsorbable implantable sheet material having an anti-microbial treatment applied thereto.

A bioabsorbable support member was constructed from a polylactic acid-polyglycolic acid co-polymer (PLA/PGA) having a weight percent ratio of 85:15, respectively. An implantable ePTFE sheet material with an anti-microbial treatment was obtained from the Medical Products Division of W. L. Gore & Associates, Inc., Flagstaff, Ariz. under the tradename GORE-TEX® DUALMESH® PLUS Biomaterial as part number 1DLMCP04. The dimensions of both components were the same so the bioabsorbable sheet member covered the implantable sheet material.

Figure 8A:
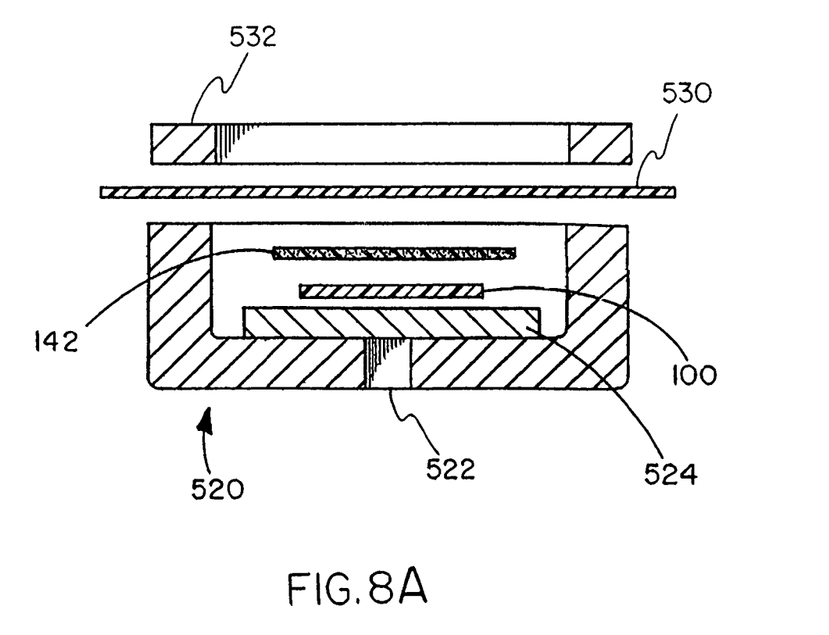
FIG. 8A illustrates a cross-sectional view of a vacuum-laminating press useful in making the present invention.

The bioabsorbable support member was attached to the implantable sheet material by placing the two component together under restraint and exerting moderate pressure (e.g., 20-50 psi) in an apparatus (FIG. 8A) to the combination. The combination was heated to a temperature between 110 degrees and 125 degrees centigrade for approximately five (5) minutes. Upon cooling of the combination under restraint and removal from the apparatus, the result was an implantable medical device of the present invention comprising a non-bioabsorbable implantable sheet material with anti-microbial properties attached to a bioabsorbable support member that is self-expandable in situ without the need for an extrinsically applied force or a thermal transition of the support member material.

What is claimed is:
1. A medical device consisting essentially of:
a resilient bioabsorbable support member comprising a first portion and a second portion and further comprising a block copolymer of polyglycolic acid and trimethylene carbonate; and
an implantable non-bioabsorbable device attached to said resilient bioabsorbable support member wherein said resilient bioabsorbable support member causes the implantable non-bioabsorbable device to change from a compacted form to a substantially planar configuration and assists in placement of said non-bioabsorbable implantable device during implantation procedures without requisite for an extrinsically applied force and wherein said implantable non-bioabsorbable device comprises a porous expanded polytetrafluoroethylene material and wherein said first portion has a bioabsorption rate that is different from the second portion.

2. The medical device of claim 1 wherein said implantable device further comprises an antimicrobial agent.

3. The medical device of claim 1 wherein said resilient bioabsorbable support member causes the implantable non-bioabsorbable device to change from a compacted form to a substantially planar configuration without a thermal transition.

4. The medical device of claim 1 wherein said implantable device has one or more markings adapted to aid visual orientation of said medical device with respect to an implantation site.

5. The medical device of claim 4 wherein said markings are located in a border area of said implantable device.

6. The medical device of claim 4 wherein said support member has one or more markings adapted to aid indirect imaging of said medical device with respect to an implantation site.

7. The medical device of claim 1 wherein said porous expanded polytetrafluoroethylene material comprises a first layer and a second layer.

8. The medical device of claim 7 wherein said first layer is sufficiently porous to permit ingrowth of cells or cellular processes therewithin and wherein said second layer does not support attachment of tissue thereto.

9. The medical device of claim 1 wherein said resilient bioabsorbable support member has a thickness sufficient to provide a tactile step.

10. The medical device of claim 1 wherein said first portion has physical dimensions that are different from said second portion.

11. The medical device of claim 10 wherein said first portion has a chemical composition different from said second portion.

12. A medical device comprising:
bioabsorbable resilient support member having a two sides, said bioabsorbable resilient support member comprising a first portion and a second portion and further comprising a block copolymer of polyglycolic acid and trimethylene carbonate; and
an implantable non-bioabsorbable device attached to one side of said resilient support member, wherein said resilient support member causes the implantable non-bioabsorbable device to change from a compacted form to a substantially planar configuration and assists in placement of said non-bioabsorbable implantable device during implantation procedures without requisite for an extrinsically applied force and wherein said implantable non-bioabsorbable device comprises a porous expanded polytetrafluoroethylene material and wherein said first portion has a bioabsorption rate that is different from the second portion.

\* \* \* \* \*